(12) United States Patent
Karpov et al.

(10) Patent No.: US 8,785,344 B2
(45) Date of Patent: Jul. 22, 2014

(54) GAS PHASE OXIDATION CATALYST WITH LOW CHARGE TRANSPORT ACTIVATION ENERGY

(71) Applicant: BASF SE, Ludwigshafen (DE)

(72) Inventors: Andrey Karpov, Metuchen, NJ (US); Cornelia Katharina Dobner, Ludwigshafen (DE); Frank Rosowski, Berlin (DE); Mark Eichelbaum, Berlin (DE); Annettte Trunschke, Berlin (DE); Robert Schloegl, Berlin (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/770,449

(22) Filed: Feb. 19, 2013

(65) Prior Publication Data

US 2013/0217896 A1    Aug. 22, 2013

Related U.S. Application Data

(60) Provisional application No. 61/600,759, filed on Feb. 20, 2012.

(51) Int. Cl.
| | | |
|---|---|---|
| *B01J 27/228* | (2006.01) | |
| *B01J 21/00* | (2006.01) | |
| *C07D 307/34* | (2006.01) | |

(52) U.S. Cl.
USPC .......................... 502/247; 502/179; 549/259

(58) Field of Classification Search
USPC .................. 502/179, 247; 549/259
See application file for complete search history.

(56) References Cited

U.S. PATENT DOCUMENTS

| | | | |
|---|---|---|---|
| 4,795,818 | A | 1/1989 | Becker et al. |
| 4,933,312 | A | 6/1990 | Haddad et al. |
| 5,093,298 | A | 3/1992 | Haddad et al. |
| 5,095,125 | A | 3/1992 | Haddad et al. |
| 5,137,860 | A | 8/1992 | Ebner et al. |
| 5,158,923 | A | 10/1992 | Barone |
| 5,275,996 | A | 1/1994 | Andrews et al. |
| 5,296,436 | A | 3/1994 | Bortinger |
| 5,641,722 | A | 6/1997 | Mitchell et al. |
| 8,323,610 | B2 | 12/2012 | Krämer et al. |
| 2003/0114688 | A1 | 6/2003 | Weiguny et al. |
| 2008/0177105 | A1 | 7/2008 | Raichle et al. |
| 2011/0230668 | A1 | 9/2011 | Altwasser et al. |
| 2011/0251052 | A1 | 10/2011 | Kramer et al. |
| 2011/0251405 | A1 | 10/2011 | Altwasser et al. |

(Continued)

FOREIGN PATENT DOCUMENTS

| | | |
|---|---|---|
| DE | 19809477 A1 | 9/1999 |
| EP | 1261424 A1 | 12/2002 |

(Continued)

OTHER PUBLICATIONS

U.S. Appl. No. 13/877,759, Karpov, Andrey.

(Continued)

*Primary Examiner* — T. Victor Oh

(74) *Attorney, Agent, or Firm* — Drinker Biddle & Reath LLP

(57) ABSTRACT

A catalyst for the gas phase oxidation of organic hydrocarbons comprises a multielement oxide which comprises at least one transition meal such as vanadium, wherein the catalyst has a charge transport activation energy $E_c$ at a temperature of 375 to 425° C. of less than 0 kJ/mol. The catalyst serves for preparation of maleic anhydride.

7 Claims, 3 Drawing Sheets

(56) References Cited

U.S. PATENT DOCUMENTS

| | | |
|---|---|---|
| 2011/0275856 A1 | 11/2011 | Karpov et al. |
| 2011/0311888 A1 | 12/2011 | Garsuch et al. |
| 2012/0004425 A1 | 1/2012 | Altwasser et al. |
| 2012/0029214 A1 | 2/2012 | Altwasser et al. |
| 2012/0095267 A1 | 4/2012 | Macht et al. |
| 2012/0149919 A1 | 6/2012 | Altwasser et al. |
| 2012/0178002 A1 | 7/2012 | Garsuch et al. |
| 2012/0264951 A1 | 10/2012 | Rosendahl et al. |
| 2012/0264952 A1 | 10/2012 | Rosendahl et al. |
| 2012/0264953 A1 | 10/2012 | Rosendahl et al. |
| 2012/0264954 A1 | 10/2012 | Rosendahl et al. |
| 2013/0023699 A1 | 1/2013 | Macht et al. |
| 2013/0109871 A1 | 5/2013 | Rosendahl et al. |

FOREIGN PATENT DOCUMENTS

| | | |
|---|---|---|
| JP | H08141403 | 4/1996 |
| WO | WO-95/26817 A1 | 10/1995 |
| WO | WO-95/29006 A1 | 11/1995 |
| WO | WO-97/12674 A1 | 4/1997 |
| WO | WO-2008/087116 A1 | 7/2008 |
| WO | WO-2011/023646 A1 | 3/2011 |

OTHER PUBLICATIONS

U.S. Appl. No. 13/672,855, Karpov, Andrey.

Hermann, J.M., et al., "In Situ Study of Redox and of p-Type Semiconducting Properties of Vanadyl Pyrophosphate and of V-P-O Catalysts During the Partial Oxidation of n-Bulane to Maleic Anhydride" Journal of Catalysis (1997) 167, pp. 106-117.

Millet, J.M.M., "Mechanism of First Hydrogen Abstraction From Light Alkanes on Oxide Catalysts" Topics on Catalysis (2006) vol. 38, pp. 83-92.

Moos, R., et al., "Direct Catalyst Monitoring by Electrical Means: An Overview on Promising Novel Principles" Topics in Catalysis (2009) 52, pp. 2035-2040.

Rouvet, F., et al., "Electrical Properties of Pure Vanadium Phosphate Phases and of VPO Catalysts used in the Partial Oxidation of n-Butane to Maleic Anhydride" Journal of the Chem. Soc. Faraday Trans., (1994) 90, pp. 1441-1448.

Sartoni, L., et al., "Gallium-doped VPO Catalysts for the Oxidation of n-butane to Maleic Anhydride" Journal of Materials CHemistry (2006) 16, pp. 4348-4360.

International Search Report for PCT/IB2013/051243, mailing date Jul. 18, 2013.

GAS PHASE OXIDATION CATALYST WITH LOW CHARGE TRANSPORT ACTIVATION ENERGY

CROSS-REFERENCE TO RELATED APPLICATIONS

This application claims benefit (under 35 USC 119(e)) of U.S. Provisional Application 61/600,759, filed Feb. 20, 2012, which is incorporated by reference.

BACKGROUND OF THE INVENTION

Transition metal-catalyzed oxygen transfer reactions are some of the most important reaction types in the chemical industry. At the forefront is the partial oxidation of hydrocarbons with molecular oxygen. Molecular oxygen in the form of atmospheric oxygen is by far the cheapest oxidizing agent. In the base state, oxygen is present as a paramagnetic triplet and is relatively unreactive. As a result of interaction with the catalyst surface, the oxygen is activated by coordination to the catalyst surface, electron transfer, dissociation of the oxygen molecule and incorporation of oxygen atoms into the oxidic crystal lattice. Lattice oxygen can be incorporated into an activated hydrocarbon by a nucleophilic addition; the oxygenated products are desorbed from the catalyst surface. The reduced catalyst surface is subsequently reoxidized by gas phase oxygen.

The oxidation of n-butane to maleic anhydride is an example of an industrially employed reaction, which requires, in a single operation, the withdrawal of eight hydrogen atoms, the incorporation of three oxygen atoms and the transfer of 14 electrons (see, for example, Millet J. M. M., *Topics on Catalysis* 2006, Vol. 38, P. 83 to 92).

It is evident from what has been stated that this demanding reaction requires a catalyst with good electronic, oxygen and/or proton conductivity. More particularly, the reaction rate for the selective oxidation of hydrocarbons can be limited by electronic and/or ionic transport properties, i.e., for example, by the transfer of electrons or holes (in other words the oxidation or reduction of the transition metal ions of the catalyst), of hydrogen or oxygen atoms from the catalyst surface to the substrate (the hydrocarbon) and vice versa, and hence places high demands on the catalyst.

One of the great challenges is the development of new catalysts with improved selectivity and/or higher conversion. The development of new catalysts, however, is very complex. One reason for this is that most of the industrial catalysts are multielement oxides which, as well as the catalytically active transition metal oxide, also comprise what are called promoters, which enhance the catalyst action and/or improve the selectivity. A shortening of the development times for new catalysts is desirable.

It is an object of the invention to provide catalysts for the gas phase oxidation of organic hydrocarbons with improved selectivity and/or higher conversion. It is another object of the invention to provide a process for optimizing a catalyst for the gas phase oxidation of organic hydrocarbons.

The invention relates to a catalyst for the gas phase oxidation of organic hydrocarbons, comprising a multielement oxide which comprises at least one transition metal, wherein the catalyst has a charge transport activation energy $E_c$ at a temperature of 375 to 425° C., especially about 400° C., of less than 0 kJ/mol (negative charge transport activation energy).

A BRIEF DESCRIPTION OF THE FIGURES

A DETAILED DESCRIPTION OF THE INVENTION

Figure 1:
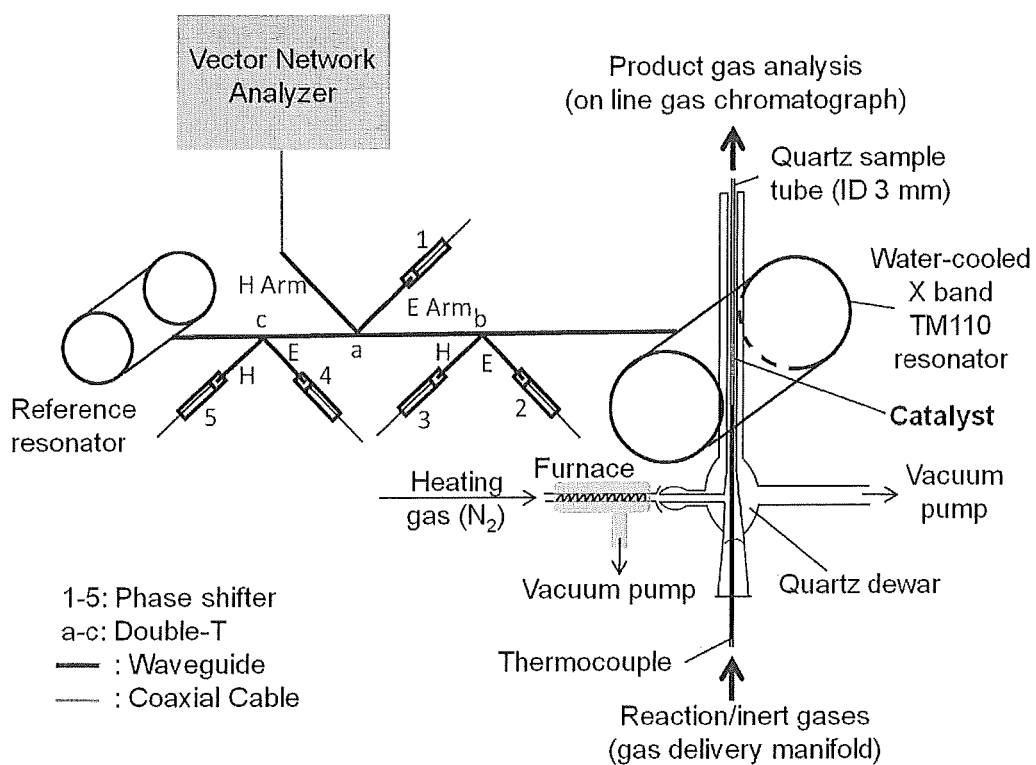
FIG. 1 shows the schematic structure of a system for contactless determination of a pulverulent catalyst by the MCPT technique.

With the invention, it has been found that what is crucial for advantageous catalytic characteristics of gas phase oxidation catalysts is not the absolute value of the electrical conductivity, but rather the charge transport activation energy $E_c$ of the catalyst. The charge transport activation energy $E_c$ can be determined on the basis of the temperature dependence of the electrical conductivity of the catalyst. It has been found that the conductivity of a gas phase oxidation catalyst within the relevant temperature range follows essentially Arrhenius behaviour. Accordingly, the charge transport activation energy $E_c$ can be determined as the plot of the natural logarithm of the conductivity of the catalyst against the reciprocal temperature.

Processes for determining the DC or AC current resistance of a sample in contact with two or four electrodes are sufficiently well known and have also already been used to determine the conductivity of catalysts; cf., for example, Hermann, J. M. et al, *Journal of Catalysis* 1997, 167, 106-117; Sartoni, L. et al, *Journal of Materials Chemistry* 2006, 16, 4348 to 4360; Rouvet, F. et al, *Journal of the Chem. Soc. Faraday Trans.*, 1994, 90, 1441 to 1448. The accuracy and reproducibility of these measurements depends greatly on the quality of the contact between the electrodes and the catalyst powder, since poor contact and hence high contact resistance considerably distort the data measured. In the case of the powder catalysts typically used, a good and reproducible contact is difficult to achieve. For the purposes of the present invention, therefore, a contactless conductivity measurement by what is called the microwave cavity enclosed perturbation technique (MCPT) is preferred. The values measured by this method are also referred to as microwave conductivity in the present context.

The charge transport activation energy $E_c$ is therefore preferably determined as the slope of the natural logarithm of the microwave conductivity at 9.2 GHz measured contactlessly for a bed of the catalyst against the reciprocal temperature.

The conductivity measurement is preferably conducted contactlessly by excitation of the catalyst with the aid of microwaves and recording of the corresponding resonance spectrum. In polycrystalline semiconductors of low conductivity which consist of conductive and insulating regions, this is because the transport of the charge carriers is usually limited by the insulating barriers at the particle boundaries of the conductive grains. The DC conductivity is thus determined principally by the height and width of the barriers at the particle boundaries, and not by the intrinsic electronic properties of the grains per se. In contrast, in the case of AC current measurements, and hence more particularly microwave measurements, the particle boundaries, with rising frequency, are increasingly bypassed by capacitative coupling between the conductive grains, and so the actual conductivity of the grains can be determined at high frequencies. Alternatively, the charge carrier transport can be described with the aid of a hopping mechanism, in which the electron conduction on the atomic scale is characterized by activated hopping of charge carriers between localized states. Both the barrier model and the hopping model describe the frequency dependence of conductivity at low frequencies with the equation $$\sigma_{AC}(\omega) = \sigma_{DC} + A\omega^s, \quad (1)$$

where s is in the range from 0 to 2 (normally close to 1), the constant A is slightly dependent on temperature and ω is the angular velocity. While the conductivity at low frequencies approximates to the DC conductivity and hence to the conductivity between the grains, it approaches the bulk conductivity of the conductive grains in the high-frequency range. Thus, measurements at microwave frequencies should be ideally suited to the determination of the intrinsic properties of polycrystalline materials, for example heterogeneous catalysts.

A great advantage of the measurements at high frequencies is that the signals can be transmitted wirelessly between transmitter and receiver and are accordingly perfectly suited to contactless processes. For this purpose, preference is given in the present context to the resonator technique because it features virtually no restrictions with regard to the shape of the sample and a very high sensitivity.

Whereas, in the case of what is called "endplate perturbation", the catalyst forms one of the endplates of the resonator, contact with the catalyst is avoided by placing it in the middle of a cavity of the microwave resonator (usually at the maximum of the electrical field; see Chen, L.-F. et al, *Microwave Electronics, Measurement and Material Characterization*, Wiley 2004, 493-530. The contactless conductivity measurement employed in the present case for heterogeneous catalysts under reaction conditions is based on what is called the microwave cavity enclosed perturbation technique (MCPT), in which the catalyst and the reactor surrounding it are disposed in the resonator.

The MCPT technique has already been applied successfully over a wide frequency range to conductivity and permittivity measurements on superconductors, superionic conductors, metals, semiconductors and dielectric materials. It is also possible to qualitatively observe the oxidation state of three-way catalytic converters from the automotive sector by using the catalyst housing as a microwave resonator and determining the resonance properties thereof in situ (Moos, R. et al., *Topics in Catalysis* 2009, 52, 2035-2040).

In the measurement, the catalyst has to be heated, whereas the cavity has to be kept at room temperature in order to avoid aging of the surface of the resonator walls and hence irrevocable worsening of the quality factor of the cavity.

A gas preferably flows over the catalyst in the conductivity measurement. The gas is preferably preheated to the respective measurement temperature. The gas may be an inert gas, such as nitrogen. The gas, however, is preferably a model reaction gas. The model reaction gas simulates the conditions under which the catalyst is used in production. A suitable model reaction gas for the preferred embodiment of a catalyst for the preparation of maleic anhydride is as follows: 2% by volume of n-butane, 20% by volume of $O_2$ and remainder $N_2$. The mass flow rate of the gas is preferably 1 to 20 ml/min.

To determine the microwave conductivity, preference is given to using a system which comprises a resonator for microwaves, within which is disposed a reactor with an accommodation site for the catalyst sample, the resonator being connected to a microwave source and the reactor being connectable at one end to a source for reaction gases and at the other end to a gas analysis apparatus.

At the same time, where a heatable source for reaction gases is provided, the catalyst sample can be heated with the aid of the reaction gases, such that only the sample and not the resonator is heated. Alternatively, it is also possible to heat the catalyst sample, rather than by heating the reaction gases, directly by a suitably selected introduced microwave power. Since, however, the microwave field here acts selectively on the dipoles in the catalyst, this alters the catalyst characteristics, which has to be taken into account in the evaluation.

The reactor may be a sample tube, for example made of quartz, in which the accommodation site is defined by suitable measures (for example delimitation by glass wool plugs) and the catalyst sample is positioned such that it comes to rest at the desired position in the resonator. Other useful reactors are flat cells (arrays).

The changes in the resonance frequency and the quality factor due to the perturbation by the quartz reactor with sample have a linear dependence on the electronic properties, which means that it is possible to determine the complex permittivity and the conductivity of the sample analyzed and hence to conduct quantitative measurements under reaction conditions, i.e., more particularly, high temperatures as necessary for catalysis reactions. This is aided by the fact that the electrical field is concentrated in the reactor consisting of a dielectric, for example quartz, and is thus amplified in the region of the sample.

The resonator can be configured according to the mode used. For instance, it is preferred that the resonator is a cylindrical X-band $TM_{mn0}$ resonator (n=0, 1, 2, . . . ; m=1, 2, . . . ), and the sample accommodation site of the reactor is disposed in the middle (along the center axis) of the resonator cavity. Preferably, n=m=1, the sample accommodation site thus being present between the local maxima of the electrical field. If the sample comes to rest between the counter-nodes (maxima) in a local minimum of the electrical field, the overall sensitivity of the system is reduced somewhat, but this can be compensated for by use of larger sample volumes, which are additionally easier to handle and to analyze. According to the size (the volume) of the cylindrical resonator, it is possible to use other TM modes, for example in the case of large resonators (r>5 cm) $TM_{0n0}$ modes (n=1, 2, 3). On the other hand, it is also conceivable to use rectangular resonators in which TE modes rather than TM modes are used for excitation, though the modes in the middle of the resonator here too may have electrical field minima. However, for the same volume, the quality of the rectangular resonator is lower than that of the cylindrical resonator. Likewise conceivable is the use of split ring resonators. Even though resonators are usable in principle for frequency ranges from 300 MHz to 300 GHz, the range from 1 to 30 GHz and especially that of 8-12 GHz (X band) is preferred in practice for conductivity measurement. Measurement at 9.2 GHz has been found to be particularly useful.

In a preferred embodiment, the system comprises an evacuated jacketed casing which is arranged around the reactor and can be connected to a vacuum source, and a heating apparatus which is connected to the reactor and introduces hot gas into it. In this way, the catalyst sample can be heated separately, i.e. without needing to be heated by the reaction gases, and the evacuated jacketed casing ensures at the same time that only the samples and not the resonator are heated. The casing is appropriately transparent to microwaves and consists, for example, of quartz glass or sapphire glass. A general requirement for the casing is low dielectric losses; in other words, the imaginary part $\in_2$ of the complex permittivity thereof must be very small. A possible design of the casing is the arrangement known as a Dewar.

The microwave sources used include, for example, klystrons, GaN diodes or vector network analyzers, and these can also detect the microwave spectrum of the excited catalyst.

In a preferred embodiment, the resonator comprises a cooling apparatus which additionally cools the walls of the resonator cavity and holds them essentially at room temperature. This particularly effectively prevents degradation of the resonator walls, which makes an essential contribution to the functioning and lifetime of the resonator, since especially the surfaces of the resonator walls have significant effects on the microwave field which forms in the resonator. In other words, the quality of the resonator can be kept constant over very long periods, which enables particularly long measurement cycles for determination of the electrical catalyst properties.

The cooling apparatus comprises, for example, a cooling water circuit which removes heat from the resonator, optionally by means of additional cooling plates. Alternatively or additionally, however, air cooling of the resonator is also conceivable, for example using large cooling bodies, for example copper masses. For avoidance of condensation water, internal ventilation of the resonator is also possible. The cooling device, however, cannot only be used for cooling of the resonator at high catalyst temperatures, but also in order to conduct measurements at low temperatures, for which the heating device is regulated correspondingly. It is thus possible, through suitable combination of heating and cooling devices, to establish any temperature conditions and temperature/time profiles under which the catalysis reaction is to be analyzed.

As already mentioned at the outset, the MCPT process is based on a slight perturbation of the resonance conditions of a cavity when a sample with a given complex permittivity and/or electrical conductivity is introduced into the cavity. In such a cavity, standing waves can form, the modes of which are characterized by a characteristic resonance frequency $v_0$ (depending on the geometry of the cavity) and the resonator quality $Q_0$ (depending on the geometry and the conductivity of the resonator wall). The quality is connected to the resonance frequency $v_0$ by what is called the half-height width $\Gamma_0$.

$$Q_0 = \frac{v_0}{\Gamma_0}, \quad (2)$$

After introduction of a small sample into the cavity, resonance frequency and the quality of the cavity change to the values $v_1$ and $Q_1$, and the corresponding shift in the values can be equated to the permittivity and the volume of the sample and of the cavity:

$$\Delta v = v_1 - v_0, \quad (3)$$

$$\frac{\Delta v}{v_0} = A(\varepsilon_1 - 1)\frac{V_s}{V_c}, \quad (4)$$

In a quasi-static approximation, in which the penetration depth of the microwaves into the surface of the sample is much greater than the dimensions of the sample, the shift in the frequency and in the quality can be equated directly to the complex permittivity $\varepsilon = \varepsilon_1 - i\varepsilon_2$ of the sample:

$$\frac{1}{Q_1} - \frac{1}{Q_0} = 2B\varepsilon_2 \frac{V_s}{V_c}, \quad (5)$$

$$\frac{1}{Q_1} - \frac{1}{Q_0} = \frac{\Gamma_1}{v_1} - \frac{\Gamma_0}{v_0}. \quad (6)$$

where A and B are resonator constants which depend on the resonator geometry and the mode, and $V_S$ and $V_C$ are the volume of the sample and of the cavity respectively. The constants A and B can in principle be calculated directly when the field distribution in the cavity is known and does not change significantly as a result of the introduction of the sample. For practical reasons, however, the resonator constants are preferably determined by analysis of suitable calibration substances with known complex permittivities which are discussed in detail hereinafter. The quasistatic approximation for insulating or poorly conducting materials is a very good approximation for the catalysts of interest at present.

Suitable permittivity standards are, for example, single crystals of sapphire (0001), sapphire (11-20), rutile (001), rutile (100), lanthanum aluminate (100) and strontium titanate (100), available from Crystal GmbH Berlin.

On the basis of a linear dependence between the complex permittivities and the shift in the resonance frequency or in the quality, a calibration curve is determined for pulverulent samples. The relationship of the dielectric properties of single crystals and pulverulent samples was calculated with the aid of the formula derived by Landau and Lifshitz (Landau/Lifshitz, *Electrodynamics of Continuous Media*; Pergamon Press, London, 1960):

$$\varepsilon_P^{1/3} - 1 = \delta(\varepsilon_B^{1/3} - 1), \quad (7)$$

where $\varepsilon_B$ and $\varepsilon_P$ are the complex permittivities of the single crystal and of the powder for a given packing density $\delta$. With the aid of this equation, it is then possible to rearrange equations (2) and (3) as follows:

$$\frac{\Delta v}{v_0} = A_p(\varepsilon_{1,p}^{1/3} - 1)\frac{V_s}{V_c}. \quad (8)$$

$$\frac{1}{Q_1} - \frac{1}{Q_0} = 2B_p \varepsilon_{2,p}^{1/3} \frac{V_s}{V_c}, \quad (9)$$

On completion of calibration, it is now possible to conduct an in situ measurement of the permittivity and of the electrical conductivity of gas phase oxidation catalysts.

The logarithm of the microwave conductivity $\sigma \cdot (\sigma = \omega \varepsilon_0 \varepsilon_2)$ is plotted as an Arrhenius plot against the reciprocal of the temperature [K]. By taking account of the exponential dependence on the reciprocal of the temperature for the electrical conductivity $$\sigma = \sigma_0 \exp\left(-\frac{E_e}{k_B T}\right), \quad (10)$$

where $\sigma_0$ is a constant, $E_c$ is the activation energy of the electrical conductivity and $k_B$ is the Boltzmann constant, the activation energy $E_c$ can be calculated from the slope of the linear regression (cf. Herrmann J. M., *Catalysis Today*, 2006, 112, 73-77). Optionally, a linear fit is effected, for example by the least squares method, in the range between 375 and 425° C.

The invention also simplifies the optimization of gas phase oxidation catalysts. For example, by variation of the preparation conditions or by combinatorial chemistry methods, it is possible to prepare a multitude of potential catalysts. The charge transport activation energy $E_c$ of the catalysts is then determined and the catalysts with improved catalytic properties are thus found.

The invention provides a process for optimizing a catalyst for the gas phase oxidation of organic hydrocarbons, which comprises a) preparing a first catalyst under a first set of preparation conditions,
b) preparing at least one further catalyst under a further set of preparation conditions,
c) determining the charge transport activation energy $E_c$ of the first and of the at least one further catalyst, and
d) identifying a catalyst having a charge transport activation energy $E_c$ of less than 0 kJ/mol as an optimized catalyst.

The preparation conditions which can be varied include the composition of the catalyst, the morphology of the catalyst, calcination conditions, formation conditions and the content in the VPO precursor of sorbed organic solvents on commencement of the calcination.

In preferred embodiments, the multielement oxide of the inventive catalyst comprises vanadium, preferably vanadium and phosphorus.

The inventive catalysts are used in a process for partial oxidation of hydrocarbons. In general, a gaseous stream comprising at least one hydrocarbon and molecular oxygen is passed over a bed of a catalyst. The conditions of the partial oxidation correspond, for example, to those which are typically used for known catalysts of the particular reaction type and are familiar to those skilled in the art.

A preferred embodiment of an inventive catalyst is a catalyst for preparation of maleic anhydride (MA). It serves for preparation of MA by gas phase oxidation of hydrocarbons having at least four carbon atoms, such as n-butane, 1-butene, i-butene, 2-isobutene, 2-trans-butene and butadiene.

The catalytically active composition of the MA catalyst comprises a phosphorus/vanadium mixed oxide (the catalyst is therefore also referred to hereinafter as VPO catalyst). The phosphorus/vanadium atomic ratio is generally 0.9 to 1.5, preferably 0.9 to 1.2, especially 1.0 to 1.1. The mean oxidation state of the vanadium is preferably +3.9 to +4.4 and more preferably 4.0 to 4.3. Such active compositions are described, for example, in U.S. Pat. No. 5,275,996, U.S. Pat. No. 5,641,722, U.S. Pat. No. 5,137,860, U.S. Pat. No. 5,095,125 or U.S. Pat. No. 4,933,312.

The inventive MA catalysts may additionally comprise promoters. Suitable promoters include the elements of groups 1 to 15 of the Periodic Table and compounds thereof. Suitable promoters are described, for example, in published specifications WO 97/12674 and WO 95/26817, and in U.S. Pat. No. 5,137,860, U.S. Pat. No. 5,296,436, U.S. Pat. No. 5,158,923 and U.S. Pat. No. 4,795,818. Preferred promoters are compounds of the elements cobalt, molybdenum, iron, zinc, hafnium, zirconium, lithium, titanium, chromium, manganese, nickel, copper, boron, silicon, antimony, tin, niobium and bismuth, more preferably of niobium, molybdenum, iron, zinc, antimony, bismuth, lithium. The promoted inventive catalysts may comprise one or more promoters. The content of the promoters is, in total, in the finished catalyst, generally not more than about 5% by weight, in each case calculated as the oxide. Preferred catalysts are those which do not comprise any promoters, and those which comprise niobium, molybdenum and/or iron.

The essential steps of the preferred catalyst preparation to form a precursor powder, shaping and subsequent calcination are explained hereinafter.

(a) Reaction of a pentavalent vanadium compound with an organic reducing solvent in the presence of a phosphorus compound while heating. This step can optionally be performed in the presence of a dispersed pulverulent support material. Preference is given to the reaction without addition of support material.

(b) Isolation of the vanadium-, phosphorus- and oxygen-comprising catalyst precursor formed ("VPO precursor"), for example by filtration or evaporative concentration.

(c) Drying of the VPO precursor at a temperature of 50 to 200° C. It is optionally possible to add pulverulent support material and/or what is called a pore former to the dried and preferably heat-treated VPO precursor powder.

(d) Shaping by conversion to the desired structure. The shaping is effected preferably by tableting, preferably with prior addition of a lubricant, for instance graphite.

(e) Calcination of the shaped VPO precursor by heating in an atmosphere comprising oxygen ($O_2$), hydrogen oxide ($H_2O$) and/or inert gas.

By varying the preparation conditions, the catalytic propensity of the catalyst can be influenced and an inventive catalyst can be obtained. It has been found that the content in the VPO precursor of sorbed organic solvents on commencement of the calcination constitutes an important influencing parameter on the charge transport activation energy $E_c$. Sorbed solvent molecules are probably converted in the course of calcination to oxidation products which can be desorbed only with difficulty, if at all, and/or sorbed solvent molecules in the course of calcination cause the formation of vanadium(III) species which can be reoxidized only with difficulty, if at all. It has therefore been found to be advantageous to subject the VPO precursor, after isolation thereof, to a solvent exchange in which the organic reducing solvent is exchanged for a volatile solvent which can be removed from the VPO precursor substantially without residue prior to the calcination. The solvent exchange is preferably repeated twice or more. With increasing number of solvent exchange cycles, the charge transport activation energy $E_c$ generally shifts to negative values.

The pentavalent vanadium compounds used may be oxides, acids and inorganic and organic salts comprising pentavalent vanadium, or mixtures thereof. Preference is given to the use of vanadium pentoxide ($V_2O_5$), ammonium metavanadate ($NH_4VO_3$) and ammonium polyvanadate (($NH_4)_2V_6O_{16}$), especially vanadium pentoxide ($V_2O_5$). The pentavalent vanadium compounds present in solid form are used in the form of a powder, preferably within a particle range from 50 to 500 μm.

The phosphorus compounds used may be reducing phosphorus compounds, for example phosphorous acid, and also pentavalent phosphorus compounds, for example phosphorus pentoxide ($P_2O_5$), orthophosphoric acid ($H_3PO_4$), pyrophosphoric acid ($H_4P_2O_7$), polyphosphoric acids of the general formula $H_{n+2}P_nO_{3n+1}$ where n≥3, or mixtures thereof. Preference is given to the use of pentavalent phosphorus compounds. Typically, the content of the compounds and mixtures mentioned is reported in % by weight, based on $H_3PO_4$. Preference is given to the use of 80 to 110% $H_3PO_4$, particular preference to that of 95 to 110% $H_3PO_4$ and very particular preference to that of 100 to 105% $H_3PO_4$.

The reducing solvent used is preferably a primary or secondary, noncyclic or cyclic, unbranched or branched, saturated alcohol having 3 to 6 carbon atoms, and mixtures thereof. Preference is given to the use of a primary or secondary, unbranched or branched $C_3$- to $C_6$-alkanol, or to the use of cyclopentanol or cyclohexanol.

Suitable alcohols include n-propanol (1-propanol), isopropanol (2-propanol), n-butanol (1-butanol), sec-butanol (2-butanol), isobutanol (2-methyl-1-propanol), 1-pentanol, 2-pentanol, 3-pentanol, 2-methyl-1-butanol, 3-methyl-1-butanol, 3-methyl-2-butanol, 2,2-dimethyl-1-propanol, 1-hexanol, 2-hexanol, 3-hexanol, 2-methyl-1-hexanol, 3-methyl-1-pentanol, 4-methyl-1-pentanol, 3-methyl-2-pentanol, 4-methyl-2-pentanol, 2,2-dimethyl-1-butanol, 2,3-dimethyl-1-butanol, 3,3-dimethyl-1-butanol, 3,3-dimethyl-2-butanol, cyclopentanol, cyclohexanol and mixtures thereof.

Very particular preference is given to n-propanol (1-propanol), n-butanol (1-butanol), isobutanol (2-methyl-1-propanol), 1-pentanol, 2-methyl-1-butanol, 3-methyl-1-butanol and cyclohexanol, especially isobutanol.

The components can be combined in different ways, for example in a stirred tank. The amount of the reducing solvent should be above the amount required in stoichiometric terms for the reduction of the vanadium from the +5 oxidation state to an oxidation state in the range of +3.5 to +4.5. In general, the amount of the reducing solvent to be added is at least such that it is sufficient for slurrying of the pentavalent vanadium compound, which enables vigorous mixing with the phosphorus compound to be added.

The slurry is heated for conversion of the compounds mentioned and formation of the catalyst precursor. The temperature range to be selected depends on various factors, more particularly the reducing action and the boiling point of the components. In general, a temperature of 50 to 200° C. and preferably of 100 to 200° C. is established. The reaction at elevated temperature generally takes several hours.

Promoter compounds can be added at any time. Suitable promoter compounds are, for example, the acetates, acetylacetonates, oxalates, oxides or alkoxides of the aforementioned promoter metals, for instance cobalt acetate, cobalt(II) acetylacetonate, cobalt(II) chloride, molybdenum(VI) oxide, molybdenum(III) chloride, iron(III) acetylacetonate, iron (III) chloride, zinc(II) oxide, zinc(II) acetylacetonate, lithium chloride, lithium oxide, bismuth(III) chloride, bismuth(III) ethylhexanoate, nickel(II) ethylhexanoate, nickel(II) oxalate, zirconyl chloride, zirconium(IV) butoxide, silicon(IV) ethoxide, niobium(V) chloride and niobium(V) oxide.

After the aforementioned thermal treatment has ended, the catalyst precursor formed is isolated, and the isolation may optionally be preceded by a cooling phase and a storage or aging phase of the cooled reaction mixture. In the isolation, the solid catalyst precursor is separated from the liquid phase. Suitable methods are, for example, filtration, decantation or centrifugation. Preference is given to isolating the catalyst precursor by filtering.

The isolated catalyst precursor is subjected to a solvent exchange ("washed"). The isolated catalyst precursor is washed with a suitable solvent in order to remove, for example, reducing agent still adhering (for example alcohol) or degradation products thereof. Suitable solvents are, for example, alcohols (e.g. methanol, ethanol, 1-propanol, 2-propanol), aliphatic and/or aromatic hydrocarbons (e.g. pentane, hexane, gasoline, benzene, toluene, xylenes), ketones (e.g. acetone, 2-butanone, 3-pentanone), ethers (e.g. 1,2-dimethoxyethane, tetrahydrofuran, 1,4-dioxane) or mixtures thereof. When the catalyst precursor is washed, preference is given to using 2-propanone, ethanol and/or methanol and particular preference to using ethanol and/or 2-propanone.

After the isolation of the catalyst precursor or after the washing, the solid is generally dried.

The drying can be performed under various conditions. In general, it is performed under reduced pressure or at atmospheric pressure. The drying temperature is generally 30 to 250° C. Preference is given to performing the drying at a pressure of 1 to 30 kPa abs and a temperature of 50 to 200° C. under oxygenous or oxygen-free residual gas atmosphere, for example air or nitrogen.

In a preferred embodiment for the shaping, the catalyst precursor powder is mixed vigorously with about 2 to 4% by weight of graphite and precompacted. The precompacted particles are tableted to give the shaped catalyst body. The use of graphite having a specific surface area of 0.5 to 5 $m^2/g$ and a particle diameter $d_{50}$ of 40 to 200 µm, as described in WO 2008/087116, is preferred.

The catalyst precursor powder can be mixed vigorously with a pore former, and treated further and shaped as described above. In general, this comprises compounds comprising carbon, hydrogen, oxygen and/or nitrogen, which are predominantly removed again by sublimation, decomposition and/or vaporization in the subsequent activation of the catalyst. Suitable pore formers are, for example, fatty acids such as palmitic acid or stearic acid, dicarboxylic acids such as oxalic acid or malonic acid, cyclodextrins or polyethylene glycols. The use of malonic acid is preferred.

The shaping is effected preferably by tableting. Tableting is a process of press agglomeration. This involves introducing a pulverulent bulk material into a pressing mold having a die between two punches and compacting it by uniaxial compression to shape it to a solid compact. This operation is divided into four sections: metering, compaction (elastic deformation), plastic deformation and ejection. The tableting is effected, for example, on rotary presses or eccentric presses.

The shaped VPO precursor is calcined within a temperature range from 250 to 600° C. by heating in an atmosphere comprising oxygen ($O_2$), hydrogen oxide ($H_2O$) and/or inert gas. Examples of suitable inert gases include nitrogen, carbon dioxide and noble gases.

The calcination can be performed batchwise, for example in a shaft furnace, staged furnace, muffle furnace or heating cabinet, or continuously, for example in a rotary tube, belt calcination furnace or rotary bulb furnace. It may comprise successive different sections in terms of temperature, such as heating, temperature holding or cooling, and successive different sections in terms of the atmospheres, for example oxygenous, steam-containing, oxygen-free gas atmospheres. Suitable calcination processes are described, for example, in U.S. Pat. No. 5,137,860 and U.S. Pat. No. 4,933,312, and the published specification WO 95/29006. Particular preference is given to continuous calcination in a belt calcination furnace having at least two, for example two to ten, calcination zones which optionally have a different gas atmosphere and a different temperature. Suitable combination, matched to the respective catalyst system, of temperatures, treatment times and gas atmospheres allows the mechanical and catalytic propensity of the catalyst to be influenced and hence controlled.

Preference is given to a calcination in which the catalyst precursor (i) is heated to a temperature of 200 to 350° C. in at least one calcination zone in an oxidizing atmosphere having an oxygen content of 2 to 21% by volume and is left under these conditions until the desired mean oxidation state of the vanadium is established; and (ii) is heated to a temperature of 300 to 500° C. in at least one further calcination zone in a nonoxidizing atmosphere having an oxygen content of less than 0.5% by volume and a hydrogen oxide content of 20 to 75% by volume, and is left under these conditions for more than 0.5 hour.

In step (i), the catalyst precursor is left in an oxidizing atmosphere having a content of molecular oxygen of generally 2 to 21% by volume and preferably of 5 to 21% by volume at a temperature of 200 to 350° C. and preferably of 250 to 350° C. over a period which is effective for establishment of the desired mean oxidation state of the vanadium. In general, in step (i), mixtures of oxygen, inert gases (e.g. nitrogen or argon), hydrogen oxide (steam) and/or air and air are used. From the point of view of the catalyst precursor conducted through the calcination zone(s), the temperature during the calcining step (i) can be kept constant, or rise or fall on average. Since step (i) is generally preceded by a heating phase, the temperature will generally rise at first in order then to settle out at the desired final value. In general, therefore, the calcination zone of step (i) is preceded by at least one further calcination zone for heating of the catalyst precursor.

The period over which the heat treatment in step (i) is maintained in the process according to the invention should preferably be selected so as to establish a mean oxidation state of the vanadium at a value of +3.9 to +4.4, preferably of +4.0 to +4.3.

Since the determination of the mean oxidation state of the vanadium during the calcination can be determined only with extreme difficulty for reasons relating to apparatus and time, the period required should advantageously be determined experimentally in preliminary tests. In general, this purpose is served by a measurement series in which heat treatment is effected under defined conditions, the samples being removed from the system after different times, cooled and analyzed for the mean oxidation state of the vanadium.

The period required in step (i) is generally dependent on the nature of the catalyst precursor, the temperature established and the gas atmosphere selected, more particularly the oxygen content. In general, the period in step (i) extends to a duration of more than 0.5 hour and preferably of more than 1 hour. In general, a period of up to 4 hours, preferably of up to 2 hours, is sufficient to establish the desired mean oxidation state. Under appropriately adjusted conditions (for example low range of the temperature interval and/or low content of molecular oxygen), however, a period of more than 6 hours may also be required.

In step (ii), the resulting catalyst intermediate is left in a nonoxidizing atmosphere having a content of molecular oxygen of less than 0.5% by volume and of hydrogen oxide (steam) of 20 to 75% by volume, preferably of 30 to 60% by volume, at a temperature of 300 to 500° C. and preferably of 350 to 450° C., over a period of more than 0.5 hour, preferably 2 to 10 hours and more preferably 2 to 4 hours. The nonoxidizing atmosphere comprises, as well as the hydrogen oxide mentioned, generally predominantly nitrogen and/or noble gases, for example argon, though this should not be understood to mean any restriction. Gases such as carbon dioxide, for example, are also suitable in principle. The nonoxidizing atmosphere preferably comprises at least 40% by volume of nitrogen. From the point of view of the catalyst precursor conducted through the calcination zone(s), the temperature during the calcination step (ii) can be kept constant, or rise or fall on average. If step (ii) is performed at a higher or lower temperature than step (i), there is generally a heating or cooling phase between steps (i) and (ii), which is optionally implemented in a further calcination zone. In order to enable an improved separation from the oxygenous atmosphere in step (i), this further calcination zone can be purged between (i) and (ii), for example for purging with inert gas, for example nitrogen. Preference is given to performing step (ii) at a temperature higher by 50 to 150° C. than step (i).

In general, the calcination comprises a further step (iii) to be performed at a time after step (ii), in which the calcined catalyst precursor is cooled in an inert gas atmosphere to a temperature below 300° C., preferably of below 200° C. and more preferably of below 150° C.

Before, during and/or after steps (i) and (ii), or (i), (ii) and (iii), further steps are possible in the calcination by the process according to the invention. Without any limiting effect, further steps include, for example, changes in the temperature (heating, cooling), changes in the gas atmosphere (switching of the gas atmosphere), further hold times, transfers of the catalyst intermediate to other apparatuses, or interruptions of the overall calcination operation.

Since the catalyst precursor generally has a temperature of <100° C. prior to commencement of the calcination, it typically has to be heated prior to step (i). The heating can be performed using various gas atmospheres. Preference is given to performing the heating in an oxidizing atmosphere as defined in step (i), or an inert gas atmosphere as defined in step (iii). An exchange of the gas atmosphere during the heating phase is also possible. Particular preference is given to heating in the oxidizing atmosphere which is also employed in step (i).

The invention further provides a process for preparing maleic anhydride, wherein a hydrocarbon having at least four carbon atoms is contacted in the presence of an oxygen-comprising gas with a bed of inventive shaped catalyst bodies. The reactors used are generally tube bundle reactors. Suitable tube bundle reactors are described, for example, in EP-B 1 261 424.

Suitable hydrocarbons in the process according to the invention are aliphatic and aromatic, saturated and unsaturated hydrocarbons having at least four carbon atoms, for example 1,3-butadiene, 1-butene, 2-cis-butene, 2-trans-butene, n-butane, $C_4$ mixture, 1,3-pentadiene, 1,4-pentadiene, 1-pentene, 2-cis-pentene, 2-trans-pentene, n-pentane, cyclopentadiene, dicyclopentadiene, cyclopentene, cyclopentane, $C_5$ mixture, hexenes, hexanes, cyclohexane and benzene. Preference is given to using propane, 1-butene, 2-cis-butene, 2-trans-butene, n-butane, benzene or mixtures thereof, especially propane, n-butane or benzene. Particular preference is given to the use of n-butane, for example in the form of pure n-butane or in the form of a component in n-butane-containing gases and liquids. The n-butane used may originate, for example, from natural gas, from steamcrackers or from FCC crackers.

The hydrocarbon is generally added under quantitative control, i.e. with constant provision of a defined amount per unit time. The hydrocarbon can be metered in in liquid or gaseous form. Preference is given to metered addition in liquid form with subsequent vaporization before entry into the tube bundle reactor unit.

The oxidizing agents used are oxygen-comprising gases, for example air, synthetic air, an oxygen-enriched gas or else what is called "pure" oxygen, for example originating from air fractionation. The oxygen-comprising gas is also added under quantitative control.

The process according to the invention is performed at a temperature of 250 to 500° C. The temperature specified is, irrespective of the type of reactor, understood in each case to mean the mean temperature of the heat carrier medium. In the case of use of n-butane as the hydrocarbon reactant, the process according to the invention is performed preferably at a temperature of 380 to 460° C. and more preferably 380 to 440° C. In the case of use of propane, the process according to the invention is executed preferably between 250 and 350° C. In the case of use of benzene, the process according to the invention is executed preferably between 330 and 450° C.

The hydrocarbon concentration of the input stream supplied to the reactor unit is 0.5 to 10% by volume, preferably 0.8 to 10% by volume, more preferably 1 to 10% by volume and most preferably 2 to 10% by volume.

The hydrocarbon conversion per reactor pass is 40 to 100%, preferably 50 to 95%, more preferably 70 to 95% and especially 85 to 95% of the hydrocarbon from the input stream.

In the process according to the invention, via the input flow rate into the reactor unit, a GHSV (gas hourly space velocity) of preferably 1000 to 10000 $h^{-1}$ and more preferably 1500 to 5000 $h^{-1}$ is established, based on the volume of the input stream supplied normalized to 0° C. and 0.1013 MPa abs, and based on the reaction volume which has been filled with catalyst or whose geometric surface area has been coated.

The reaction products or the product stream can optionally be diluted by adding substances inert under the reaction conditions, for example water or nitrogen, at the end of the reactor or at the reactor outlet, so as to obtain a non-explosive product stream. In addition, it is advantageously possible to achieve a non-explosive product stream by means of a pressure stage. This product stream can then be processed by the conventional workup units.

The invention is illustrated in detail by the appended drawings and the examples which follow.

FIG. 1 shows the schematic structure of a system for contactless determination of a pulverulent catalyst by the MCPT technique.

Figure 2:
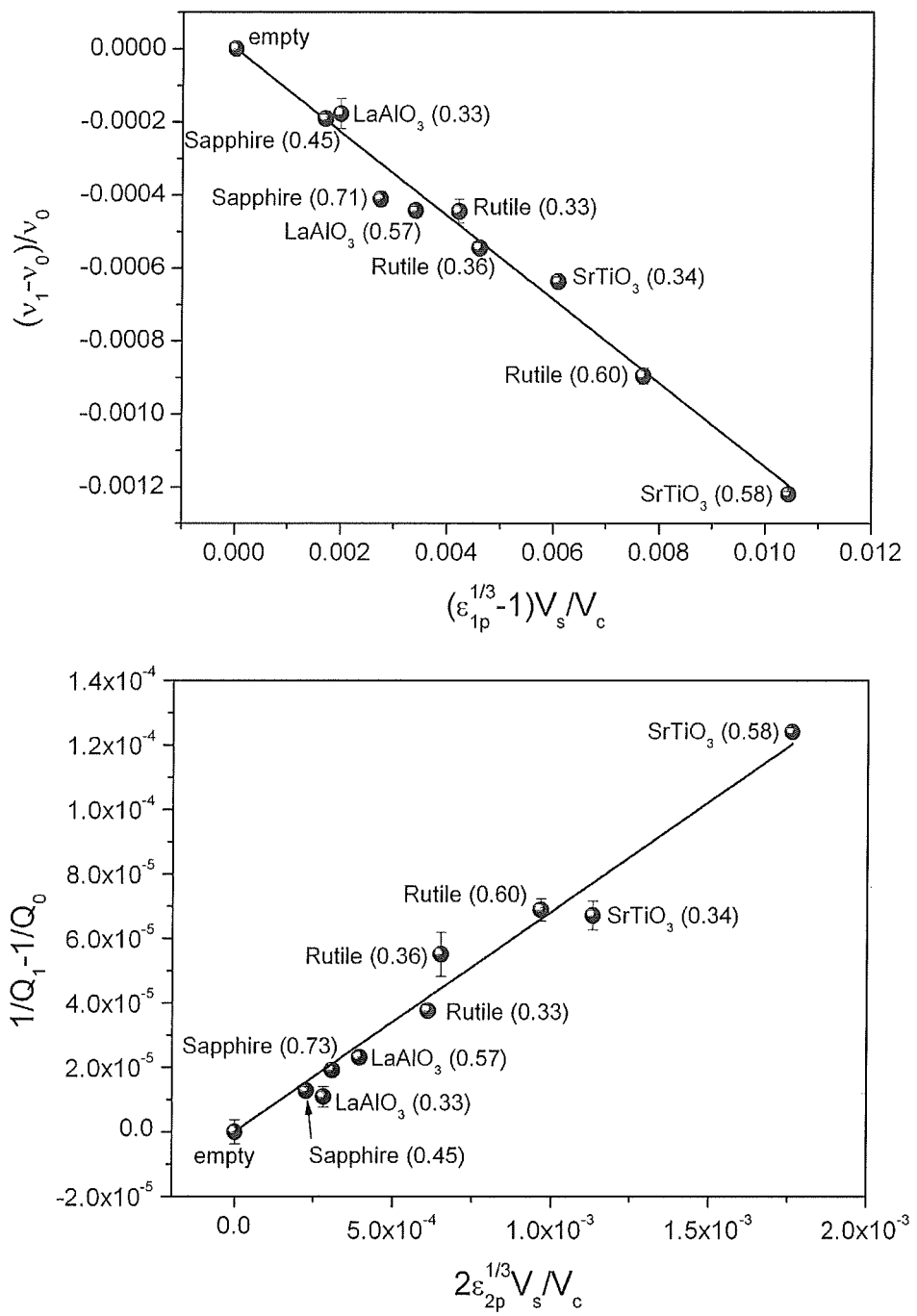
FIG. 2 shows a calibration curve of the system of FIG. 1 with various pulverulent permittivity standards.

FIG. 2 shows a calibration curve of the system of FIG. 1 with various pulverulent permittivity standards.

Figure 3:
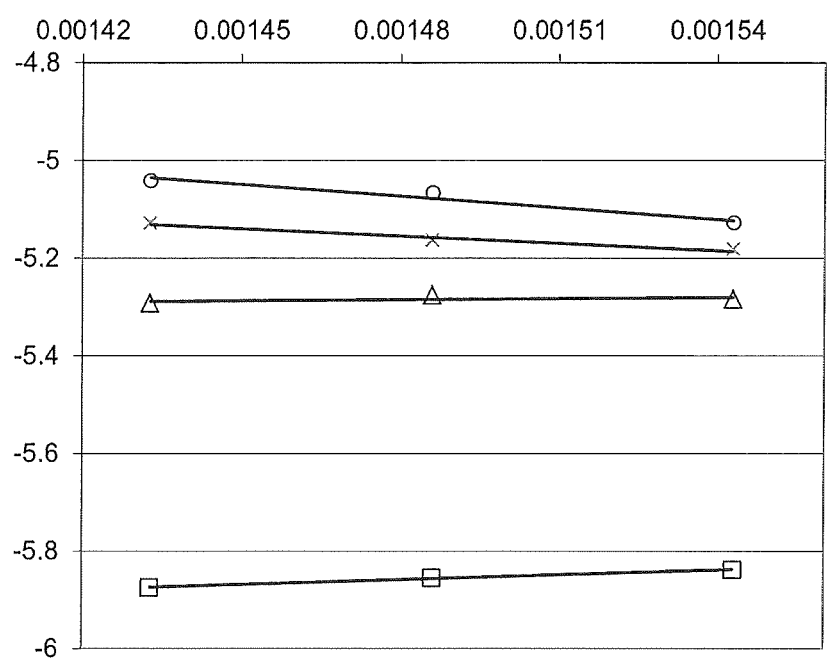
FIG. 3 shows the plot of the natural logarithm of the microwave conductivity (the ordinate) against the reciprocal temperature (the abscissa) for various catalysts.

FIG. 3 shows the plot of the natural logarithm of the microwave conductivity (the ordinate) against the reciprocal temperature (the abscissa) for various catalysts.

EXAMPLES

Four VPO catalysts were prepared as follows:
Preparation of the Catalyst Precursors Example A1

Preparation of the VPO Precursor

A nitrogen-inertized 3 l stirred vessel (1-level impeller stirrer, baffles with $d_a$=10 mm) was initially charged with 2000 ml of isobutanol. Subsequently, 287.9 g of polyphosphoric acid (105%, from Thermphos) were added while stirring (300 rpm). The mixture was homogenized within 10 minutes. Subsequently, 218.3 g of vanadium pentoxide (from GfE) and 53.9 g of vanadiumoxy triethoxide (from Sigma-Aldrich) were added to the mixture. The resulting suspension was heated to a temperature of 100.5-104° C. under reflux within 45 minutes and left under these conditions for 16 hours. The mixture was cooled to a temperature of 45° C. within 40 minutes. Thereafter, the hot suspension was transferred to a suction filter (pore size 4) and filtered at a pressure of up to 77 MPa abs. After 120 minutes, the filtercake was transferred back into the reaction vessel and suspended with 1500 ml of ultrapure (denatured) ethanol and heated to reflux (T=75-78° C.) at 200 rpm and left under these conditions for 1 hour. The mixture was cooled to a temperature of 25° C. within 60 minutes. Thereafter, the suspension was transferred to a suction filter (pore size 4) and filtered at a pressure of up to 77 MPa abs. After 30 minutes, the filtercake was transferred back into the reaction vessel again. This solvent exchange was conducted a total of 5 times, until the mother liquor (filtrate) had an isobutanol concentration of <2% by weight (detection by GC analysis). Thereafter, the filtercake was transferred into a porcelain dish and comminuted with a spatula. The product was subsequently heated to 150° C. in a vacuum drying cabinet and dried at a pressure of 77 mbar abs for 16 hours.

Comparative Example B1

Preparation of the VPO Precursor

A nitrogen-inertized 3 l stirred vessel (1-level impeller stirrer, baffles with $d_a$=10 mm) was initially charged with 2000 ml of isobutanol. Subsequently, 287.9 g of polyphosphoric acid (105%, from Thermphos) were added while stirring (300 rpm). The mixture was homogenized within 10 minutes. Subsequently, 218.3 g of vanadium pentoxide (from GfE) and 53.9 g of vanadiumoxy triethoxide (from Sigma-Aldrich) were added to the mixture. The resulting suspension was heated to a temperature of 100.5-104° C. under reflux within 45 minutes and left under these conditions for 16 hours. The mixture was cooled to a temperature of 45° C. within 40 minutes. Thereafter, the hot suspension was transferred to a suction filter (pore size 4) and filtered at a pressure of, up to 77 MPa abs. After 120 minutes, the filtercake was transferred into a porcelain dish and comminuted with a spatula. The product was subsequently heated to 150° C. in a vacuum drying cabinet and dried at a pressure of 10 mbar abs for 16 hours.

Example A2

Preparation of the $Nb_{0,1}$VPO Precursor

A nitrogen-inertized 3 l stirred vessel (1-level impeller stirrer, baffles with $d_a$=10 mm) was initially charged with 1800 ml of isobutanol. Subsequently, 287.9 g of polyphosphoric acid (105%, from Thermphos) were added while stirring (300 rpm). The mixture was homogenized within 10 minutes. Subsequently, 242.6 g of vanadium pentoxide (from GfE) and 84.88 g of niobium ethoxide (from Sigma-Aldrich, purity 95%) were added to the mixture. The resulting suspension was processed further analogously to Example A1.

Comparative Example B2

Preparation of the $Nb_{0,1}$VPO Precursor

A nitrogen-inertized 3 l stirred vessel (1-level impeller stirrer, baffles with $d_a$=10 mm) was initially charged with 1800 ml of isobutanol. Subsequently, 287.9 g of polyphosphoric acid (105%, from Thermphos) were added while stirring (300 rpm). The mixture was homogenized within 10 minutes. Subsequently, 242.6 g of vanadium pentoxide (from GfE) and 84.88 g of niobium ethoxide (from Sigma-Aldrich, purity 95%) were added to the mixture. The resulting suspension was processed further analogously to Example B1.

Preparation of the Catalysts

The dried powders obtained from examples A1-A2 and comparative examples B1-B2 were comminuted to a particle size of <500 μm on a round sieve and transferred into a porcelain dish. The product was subsequently heated to 250° C. in a forced-air oven and heat treated under 800 l (STP)/h of air for 5 hours. After cooling to room temperature, the catalyst precursor was mixed intimately with 1% by weight of graphite (Timrex T44) and processed to spall on a compacting machine (Powtec RCC 100*20, pressure=200 bar, sieving mill 110.7, roller 2.4, screw 16). The spall was sieved to a fraction of 0.5 to 1 mm.

20 g of the spall were introduced into an electrically heated tube and heated with air (25 l (STP)/h) to a temperature of 250° C. at a heating rate R1 of 5° C./min and left at this temperature for a hold time of 50 minutes. Then the gas atmosphere was switched to a mixture of 25% by volume of air, 25% by volume of nitrogen and 50% by volume of steam (total flow rate of the gas atmosphere G2 was 25 l (STP)/h) and the spall was heated to a temperature of 370° C. at a heating rate of 1° C./min and left at this temperature for a hold time of 5 minutes. Subsequently, the gas atmosphere was switched to a mixture of 50% by volume of nitrogen (12.5 l (STP)/h) and 50% by volume of steam (12.5 l (STP)/h) and the spall was heated to a temperature of 425° C. at a heating rate of 3° C./min and held at this temperature for a hold time of 195 minutes. Subsequently, the gas atmosphere was switched to nitrogen (25 l (STP)/h) and the spall was cooled to room temperature.

Equilibration of the Catalysts

Inventive catalysts A1-A2 and comparative catalysts B1-B2 were equilibrated over 1 ml of the sample in each case in a 48-tube test reactor as described in DE 198 09 477 A1. The composition of the reaction gas mixture is defined by the concentration of n-butane, air, steam and triethyl phosphate. The difference from 100% by volume consisted of argon.

$x_{n\text{-}butane}$=butane concentration of the input stream
$x_{air}$=air concentration of the input stream
$x_{Ar}$=argon concentration of the input stream
$x_{H2O}$=steam concentration of the input stream
$x_{TEP}$=triethyl phosphate concentration of the input stream
GHSV=flow rate of the input stream, based on the volume of the supplied input stream normalized to 0° C. and 0.1013 MPa abs, and based on the reaction volume filled with catalyst
T=reactor temperature

TABLE 2

Equilibration conditions of the catalysts

| Time [h] | $x_{n\text{-}butane}$ [% by vol.] | $x_{air}$ [% by vol.] | $x_{H2O}$ [% by vol.] | $x_{TEP}$ [ppm by vol.] | GHSV [h$^{-1}$] | T [° C.] |
|---|---|---|---|---|---|---|
| 12 | 1    | 92.63 | 3 | 0 | 1700 | 380 |
| 12 | 1.5  | 92.63 | 3 | 0 | 1700 | 380 |
| 12 | 1.7  | 92.63 | 3 | 1 | 2000 | 380 |
| 24 | 1.95 | 92.63 | 3 | 1 | 2000 | 380 |
| 60 | 1.95 | 92.63 | 3 | 1 | 2000 | 400 |
| 12 | 1.95 | 92.63 | 3 | 1 | 2000 | 350 |
| 12 | 1.95 | 92.63 | 3 | 1 | 2000 | 375 |
| 12 | 1.95 | 92.63 | 3 | 1 | 2000 | 400 |
| 12 | 1.95 | 92.63 | 3 | 1 | 2000 | 420 |
| 12 | 1.95 | 92.63 | 3 | 1 | 2000 | 450 |
| 12 | 1.95 | 92.63 | 3 | 1 | 5000 | 450 |
| 12 | 1.95 | 92.63 | 3 | 1 | 5000 | 420 |
| 12 | 1.95 | 92.63 | 3 | 1 | 5000 | 400 |
| 12 | 1.95 | 92.63 | 3 | 1 | 5000 | 375 |
| 12 | 1.95 | 92.63 | 3 | 1 | 5000 | 350 |
| 12 | 1.95 | 92.63 | 3 | 1 | 2000 | 400 |

Conductivity Measurement by the MCPT Technique

The equilibrated catalysts were transferred into a conductivity measurement system. The conductivity measurement system used is shown schematically in FIG. 1. A cylindrical X-band resonator 2' with a TM$_{110}$ cavity and a height of 19.5 mm and a diameter of 38.5 mm was used. Such a resonator is obtainable, for example, from Bruker BioSpin.

In the middle between the end plates 2a' and 2b' of the cylindrical resonator 2', a reactor tube 3 is conducted through the resonator cavity in radial direction, the reactor tube 3 being surrounded by a quartz Dewar 5 which is connected by connections 5a, 5b to vacuum suction (outer Dewar volume) and a hot gas source (inner Dewar volume). A heat source (oven) 8 is provided on the hot gas feed line, and brings the nitrogen gas N$_2$ introduced and, as a result, the sample P held in the nitrogen gas stream to the reaction temperature.

The reactor tube 3 has an internal diameter of 3 mm and an external diameter of 4 mm and comprises, at its sampling point 4, the pulverulent catalyst sample P which is in turn held by two glass wool plugs (not shown) in a position on the longitudinal axis of the resonator. The height of the pulverulent sample in this example is about 10 mm. The quartz Dewar, more specifically the tubular part thereof introduced into the resonator, has an external diameter of 10 mm and is, together with the sample tube, postioned in the interior thereof, at right angles to the waveguide connected to the resonator cavity.

The reactor tube is connected in the upstream direction to a reaction gas supply connection 5c with mass flow controllers (Bronkhorst El-Flow) and downstream to an on-line gas chromatograph GC (Agilent 7890A). For quantitative analysis, the gas stream is divided into a first gas stream for analysis of CO$_2$, H$_2$O, n-butane, N$_2$, O$_2$ and CO, and a second gas stream for analysis of maleic anhydride (product). The individual gases in the first gas stream are separated by a Poraplot column (CO$_2$, H$_2$O, C$_4$H$_{10}$) and a molecular sieve (N$_2$, O$_2$ and CO), and analyzed with the aid of a thermal conductivity sensor. The maleic anhydride in the second gas stream was separated from the reaction mixture by a DB1 column and detected by a flame ionization detector.

The oven 8 is configured as a resistance oven (Sylvania Tungsten Series I) and delivered eight liters per minute of preheated nitrogen for heating of the catalyst sample P to temperatures between room temperature and 500° C. To avoid condensation liquid, all connecting lines between reactor and GC are heated to 150° C. The evacuation of the quartz Dewar to 10$^{-7}$ mbar was effected with the aid of a Pfeiffer HiCube 80 Eco pump. The cavity is additionally water-cooled with the aid of a two-circuit cooling system via copper plates mounted on the resonator end plates.

The resonator cavity was coupled via an aperture to a waveguide 11 which has been connected via coaxial cable 10 to a vector network analyzer 9 (VNA, Agilent PNA-L N5230C-225 with operating range between 10 MHz and 20 GHz), in order to record the resonance spectra of what are called the S11 parameters in reflection mode (reflected power as a function of frequency). The microwave output power was 11 dBm and the resonance frequency was measured directly by determining the frequency at the minimum of the S11 parameter spectrum. The Q factor (quality) was determined by measuring the frequency difference in the resonance peaks at a 3 dB power absorption level (FWHM) and multiplying the reciprocal bandwidth determined by the resonance frequency. The critical coupling of the microwave into the resonator was adjusted by means of phase shifters 12 and monitored by means of the Smith chart representation of the VNA 9. For independent checking of the frequency of the microwave source in the VNA 9, a reference resonator 13 is additionally connected to the waveguide 11.

The permittivity standards used were single crystals of sapphire (0001), sapphire (11-20), rutile (001), rutile (100), lanthanum aluminate (100) and strontium titanate (100), obtainable from Crystal GmbH Berlin. The permittivity standards were ground to pulverulent samples. A calibration curve was then determined for pulverulent samples, measuring different packing densities of the calibration samples. The results are shown in FIGS. 2a) and 2b), in each case for the shift in resonance frequency (calibration constant $A_p$= −0.115±0.005) and the shift in the quality (calibration constant $B_p$=0.067+0.003).

The catalyst samples P were ground to powders of particles of 100 to 200 μm in size. For the MCPT measurements, 75 mg of a fraction, which passed through a sieve, of particles of the VPO catalyst of 100 to 200 μm in size were introduced into the quartz reactor tube up to a sample fill height of 10 mm. Then the temperature dependence of the complex permittivity was measured, for which the catalyst was heated from 25° C. to 416° C. at a heating rate of 10° C./min, while the sample was flushed with 5 ml/min of reaction gas mixture (2% by volume of n-butane, 20% by volume of $O_2$ and remainder $N_2$). At the same time, the resonance frequency and quality were established at different temperatures after an isothermal hold time of 10 min in each case.

The $\in_2$ values were used to calculate the electrical conductivity σ. The logarithm of σ was plotted against the reciprocal temperature. The results for the three catalysts studied, at temperatures of 375, 400 and 425° C., are shown in FIG. 3 (squares—measured values for catalyst A1, triangles—measured values for catalyst A2, crosses—measured values for catalyst B1, circles—measured values for catalyst B2).

The activation energies determined therefrom in the temperature range from 375° C. to 425° C. and the results of the catalytic tests for the catalysts studied at a temperature of 400° C. are as follows:

| Catalyst | MA yield [mol %] | Activation energy [kJ/mol] |
|---|---|---|
| A1 | 54 | −2.7 |
| A2 | 45 | −1.1 |
| B1 | 33 | +4.1 |
| B2 | 29 | +6.6 |

The invention claimed is:

1. A catalyst for the gas phase oxidation of organic hydrocarbons, comprising a multi-element oxide which comprises at least one transition metal, wherein the catalyst has a charge transport activation energy $E_c$ at a temperature of 375 to 425° C. of less than 0 kJ/mol.

2. The catalyst according to claim 1, wherein the charge transport activation energy $E_c$ is determined as the slope of the natural logarithm of the microwave conductivity at 9.2 GHz measured contactlessly for a bed of the catalyst against the reciprocal temperature.

3. The catalyst according to claim 1, wherein the multi-element oxide comprises vanadium.

4. The catalyst according to claim 1, wherein the multi-element oxide comprises vanadium and phosphorus.

5. A process for partial oxidation of hydrocarbons, which comprises passing a gaseous stream comprising at least one hydrocarbon and molecular oxygen over a bed of the catalyst according to claim 1.

6. The process according to claim 5 for preparation of maleic anhydride, wherein the gaseous stream comprises at least one hydrocarbon selected from the group consisting of n-butane, 1-butene, i-butene, 2-isobutene, 2-transbutene and butadiene.

7. A process for optimizing a catalyst for the gas phase oxidation of organic hydrocarbons, said process comprising:
   a) preparing a first catalyst under a first set of preparation conditions, wherein the first set of preparation conditions comprises:
      (1) reacting a pentavalent vanadium compound with an organic reducing solvent in the presence of a phosphorus compound while heating to produce a vanadium-, phosphorus-, and oxygen-comprising catalyst precursor ("VPO precursor");
      (2) isolating the VPO precursor;
      (3) drying the VPO precursor at a temperature of 50 to 200° C.;
      (4) shaping by conversion to the desired structure; and
      (5) calcining the shaped VPO precursor by heating in an atmosphere comprising oxygen ($O_2$), hydrogen oxide ($H_2O$), and/or inert gas;
   b) preparing at least one further catalyst under a varied set of preparation conditions, wherein one or more of the following reaction conditions is varied:
      the composition of the catalyst;
      the morphology of the catalyst;
      the calcination conditions;
      the formation conditions; and
      the content in the VPO precursor of sorbed organic solvents on commencement of the calcination
   c) determining the charge transport activation energy $E_c$ of the first and of the at least one further catalyst, and
   d) identifying a catalyst having a charge transport activation energy $E_c$ of less than 0 kJ/mol as an optimized catalyst.

* * * * *